US009194417B2

(12) United States Patent
Marchand et al.

(10) Patent No.: US 9,194,417 B2
(45) Date of Patent: Nov. 24, 2015

(54) SCREWABLE ELEMENT FOR FASTENING A CONDUIT TO A COUNTER-PIECE

(75) Inventors: Claude Louis Marchand, Hoelstein (CH); Christian Fehr, Itingen (CH); Katrin Maier Fehr, legal representative, Itingen (CH)

(73) Assignee: Labomatic Instruments AG, Allschwil (CH)

( * ) Notice: Subject to any disclaimer, the term of this patent is extended or adjusted under 35 U.S.C. 154(b) by 0 days.

(21) Appl. No.: 14/130,984

(22) PCT Filed: Jul. 5, 2012

(86) PCT No.: PCT/EP2012/063162
§ 371 (c)(1),
(2), (4) Date: Jul. 28, 2014

(87) PCT Pub. No.: WO2013/004789
PCT Pub. Date: Jan. 10, 2013

(65) Prior Publication Data
US 2014/0334894 A1 Nov. 13, 2014

(30) Foreign Application Priority Data
Jul. 6, 2011 (DE) .......... 10 2011 106 696

(51) Int. Cl.
F16B 31/00 (2006.01)
F16B 31/04 (2006.01)
F16B 31/02 (2006.01)
F16L 19/028 (2006.01)
F16L 47/04 (2006.01)
G01N 30/60 (2006.01)

(52) U.S. Cl.
CPC .............. *F16B 31/04* (2013.01); *F16B 31/027* (2013.01); *F16L 19/0286* (2013.01); *F16L 47/04* (2013.01); *G01N 30/6004* (2013.01)

(58) Field of Classification Search
CPC .......... F16B 31/00; F16B 31/02; F16B 31/04; F16B 31/024; F16B 31/027; F16B 31/028; F16L 47/04
USPC .............................. 411/1, 3, 5, 6, 7
See application file for complete search history.

(56) References Cited

U.S. PATENT DOCUMENTS

| 3,368,602 | A | * | 2/1968 | Boyd | 411/105 |
| 3,425,314 | A | * | 2/1969 | Ohlson | 411/7 |
| 4,687,392 | A | * | 8/1987 | Bidwell | 411/6 |
| 4,784,549 | A | * | 11/1988 | Wing | 411/1 |
| 5,779,409 | A | * | 7/1998 | Manzolli | 411/7 |
| 5,967,721 | A | * | 10/1999 | Giachinta et al. | 411/7 |
| 6,309,154 | B1 | * | 10/2001 | Higgins | 411/7 |
| 6,557,900 | B1 | * | 5/2003 | Austin | 285/92 |
| 6,981,882 | B1 | * | 1/2006 | Palaniappa | 439/73 |
| 2003/0152439 | A1 | * | 8/2003 | Hartmann et al. | 411/161 |
| 2004/0165966 | A1 | * | 8/2004 | Aukzemas et al. | 411/353 |
| 2012/0099943 | A1 | * | 4/2012 | Chiu | 411/347 |

\* cited by examiner

*Primary Examiner* — Roberta Delisle
(74) *Attorney, Agent, or Firm* — Leech Tishman Fuscaldo & Lampl; Kenneth D'Alessandro, Esq.

(57) ABSTRACT

A screw element for fastening an article to a counter-piece, including a first part rotatable by hand or with a tool and a second part provided with a thread, wherein the first part and the second part can be rotated relative to one another about a longitudinal axis of the screw element, but can be held axially to one another via a connection point, as well as being composed of an installation limiting a torque transferred from the first part to the second part, the installation having at least one ramp part which can rotate with the first part or with the second part in a direction in parallel to the longitudinal axis of the screw element with respect to a spring bias and cooperating with ratchet noses of the respective other one of the first part or the second part.

19 Claims, 8 Drawing Sheets

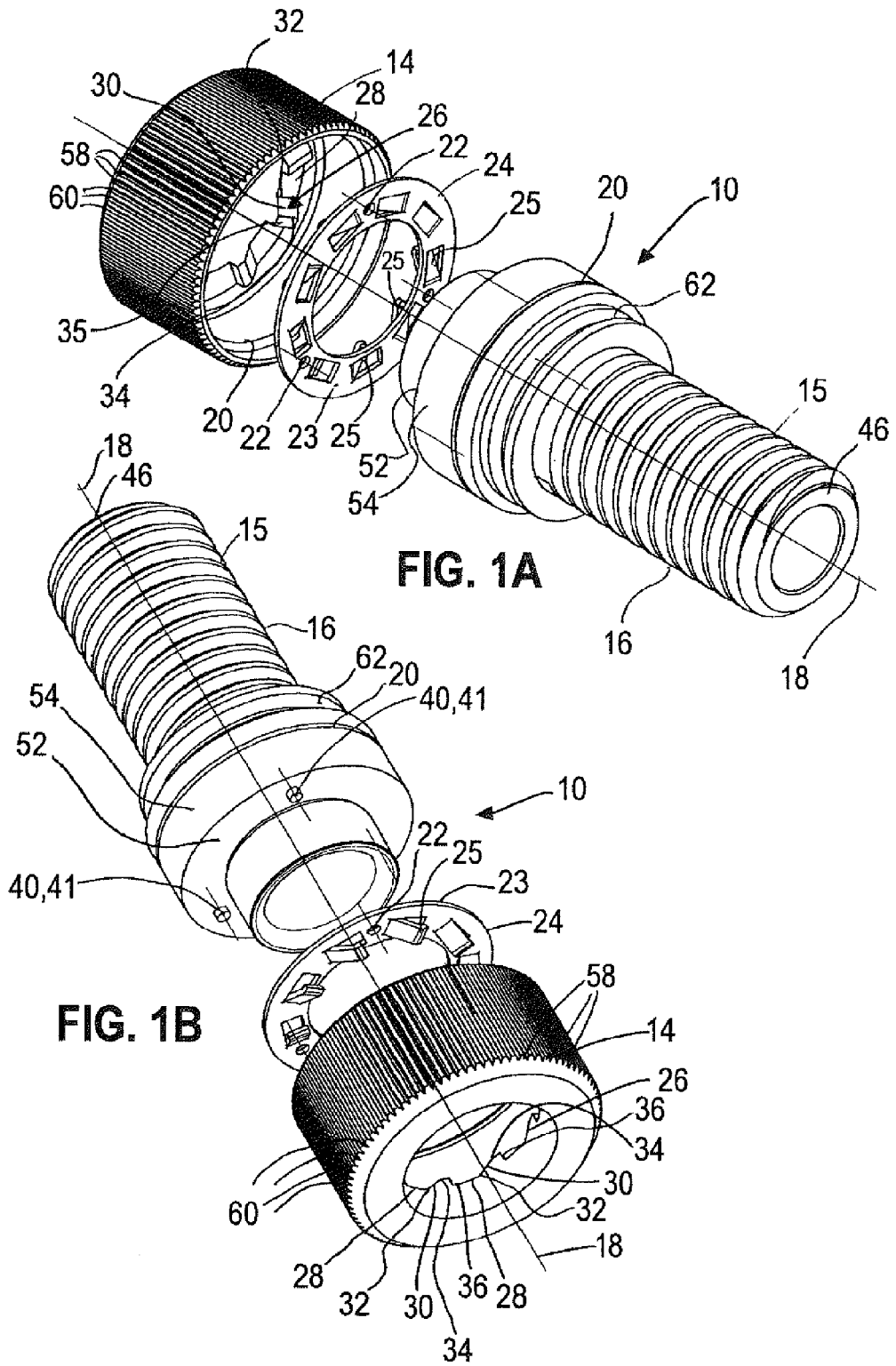

Figure 2A:
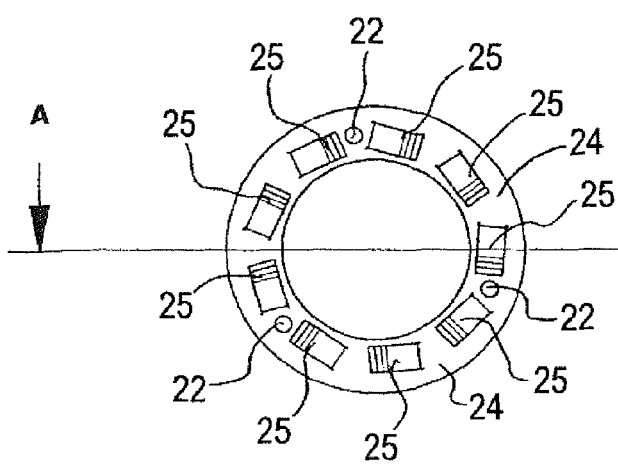
Figure 2B:
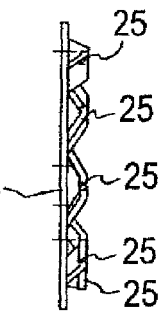
Figure 2C:
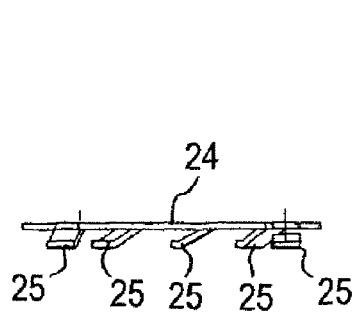
Figure 2D:
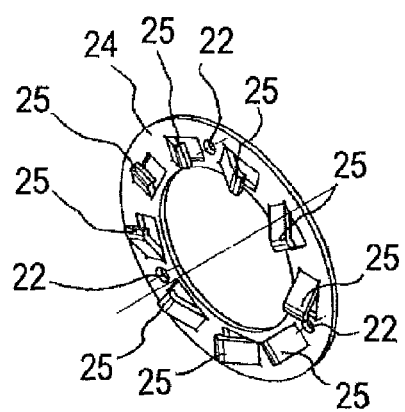

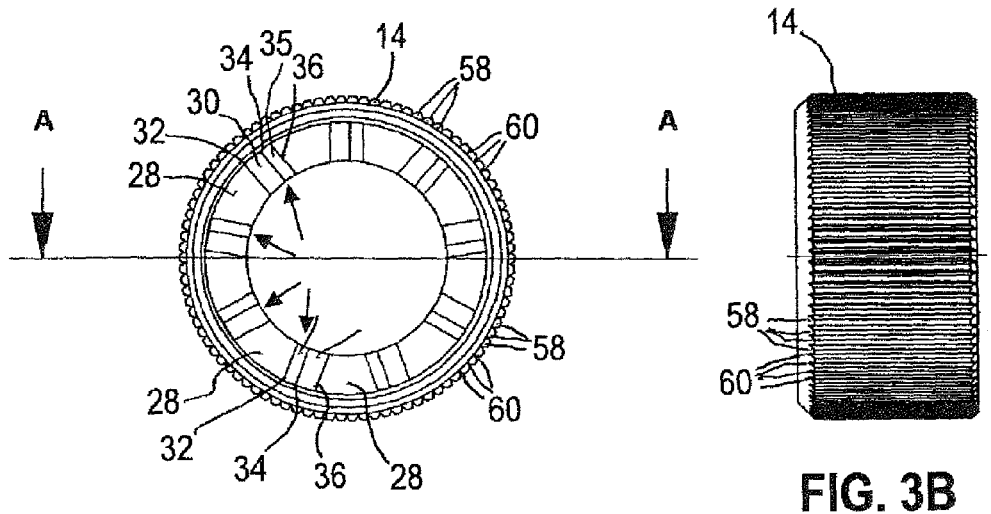
FIG. 3A
FIG. 3B
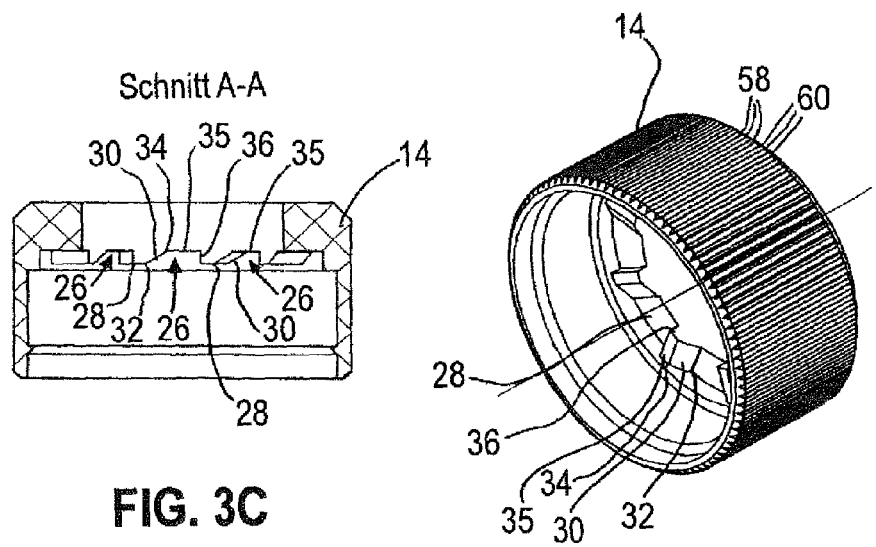
Schnitt A-A
FIG. 3C
FIG. 3D

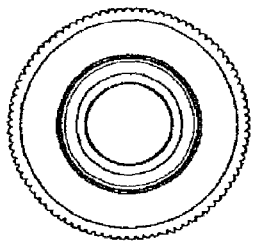
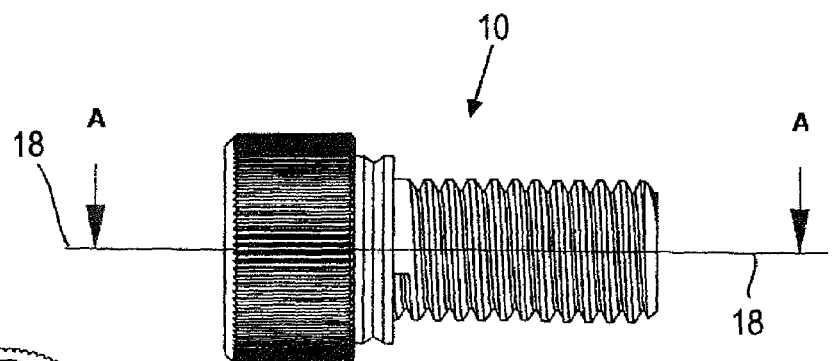
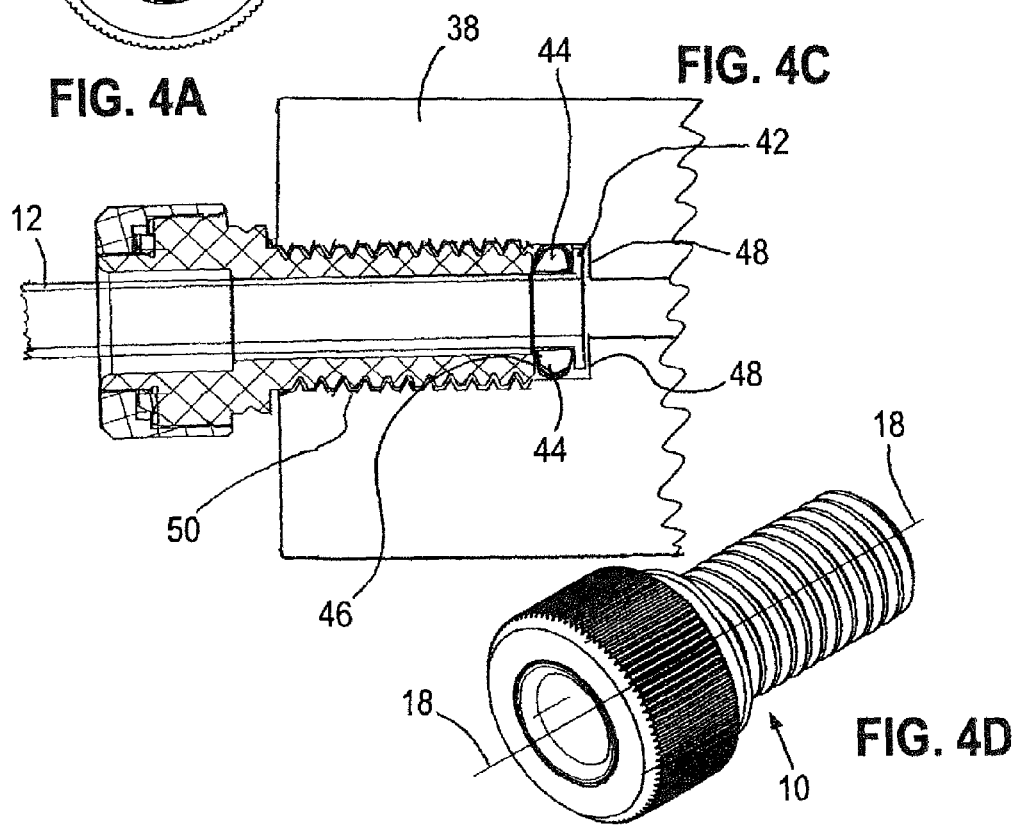
FIG. 4A
FIG. 4B
FIG. 4C
FIG. 4D

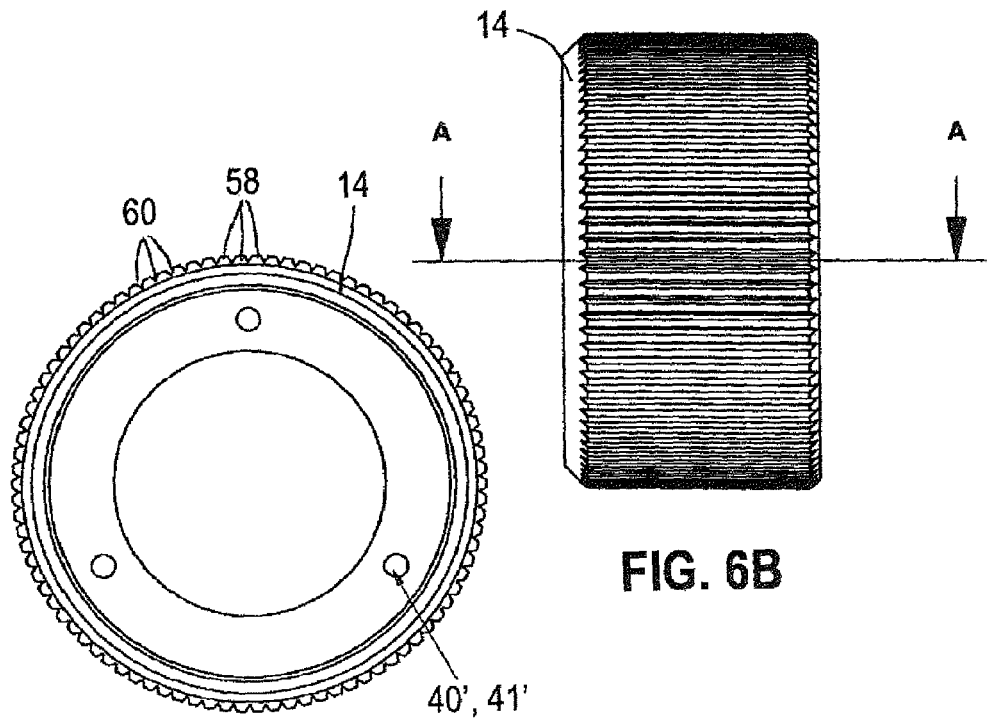
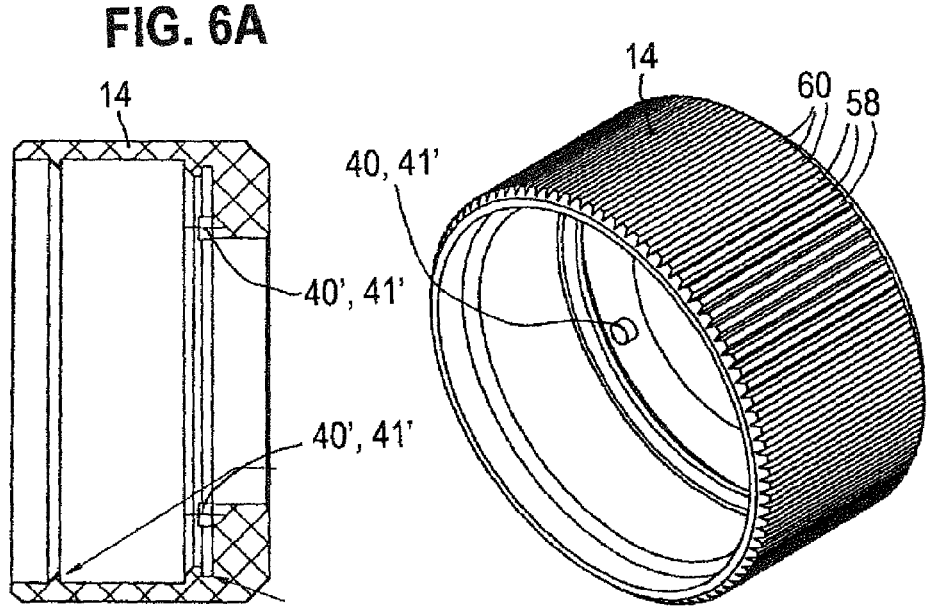

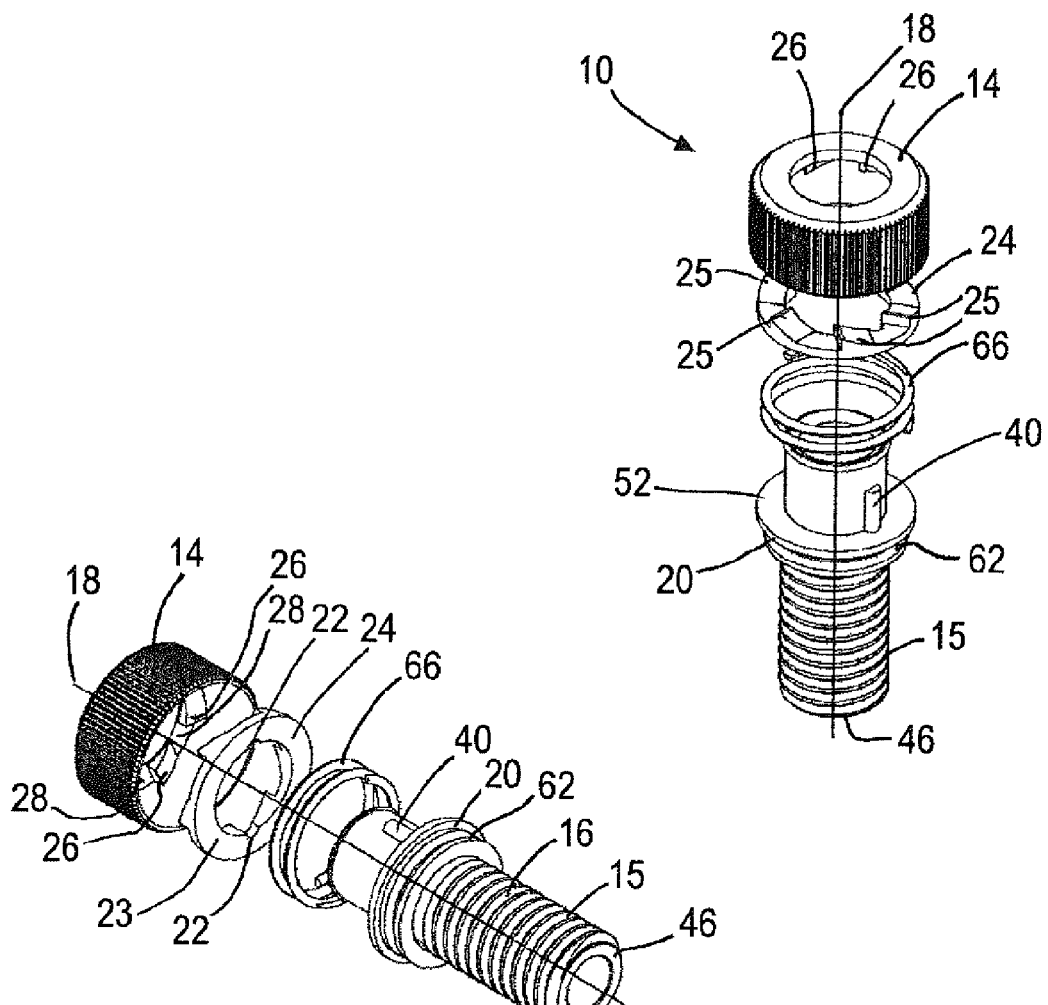

SCREWABLE ELEMENT FOR FASTENING A CONDUIT TO A COUNTER-PIECE

CROSS-REFERENCE TO RELATED APPLICATIONS

This application is the United States national phase of International Application No. PCT/EP2012/063162 filed Jul. 5, 2012, and claims priority to German Patent Application No. 10 2011 106 696.2 filed Jul. 6, 2011, the disclosures of which are hereby incorporated in their entirety by reference.

The present invention relates to a screw element for fastening an article, for example having the shape of a plastic line, to a counter-piece, such as a connector to a further line or a device connection, wherein the screw element is composed of a first part rotatable by hand or with a tool and of a second part provided with a thread, wherein the first part and the second part can be rotated relative to one another about the longitudinal axis of the screw element, but can be held axially to one another via a connection point, as well as being composed of an installation limiting a torque transferred from the first part to the second part.

Screw elements which serve for the fastening of a line to a counter-piece, be it to a connector to a further line or to a connection at a housing of a device or to a pneumatic or hydraulic installation, are known in a large variety. The connections can be inputs or outputs. The lines can be composed of metal and/or of plastic and can be rigid or flexible. The screw elements can have the shape of hollow bolts or of screw sockets or can be configured as sleeve nuts. Also screw elements are used for fastening electric lines to electric devices. Such screw elements frequently have the shape of hollow screw bolts which comprise a ring-shaped sealing element and/or a clamping element for the line, as well as having the line guided through the sealing element. The lines composed of plastic are frequently molded over towards the outside in order to form a flange which simultaneously acts as a seal. The screw element generally presses against a support ring with its end face which support ring in turn directly, or via a seal, presses against the flange and presses this against the base surface of a connecting bore. In particular for lines which are composed of PTFE or of FEP the pressing pressure at the flange thus has to be maintained within certain limits, since otherwise the plastic material begins to flow in an undesired manner.

In particular in the field of the analytical, preparatory or industrial chromatography and in the field of medical diagnostics and for laboratory devices in general relatively thin hoses of plastic, which in operation are frequently subjected to a high pressure, are frequently connected to the corresponding devices by means of screw elements of plastic, for example, to HPLC devices, MPLC devices or LPLC devices and/or to chromatography columns. In this connection a considerable number of lines can be connected to a device. Generally the screw elements are tightened by hand, this means they are tightened by means of fingers. However, it can happen that the accessibility of the screw elements is difficult due to the limited spatial conditions. In this connection, it can indeed happen that corresponding screw elements can only ever be turned over small angular ranges and it can be necessary to use a tool in order to sufficiently tighten the screw elements. Regardless of whether the screw elements are tightened by hand or with a tool, it is appropriate to ensure that the screw elements are tightened sufficiently, however, not so tight that the thread of the screw element, which is frequently composed of plastic, is damaged or that the screw elements are tightened so hard that the seal of the plastic hose is no longer ensured, be it due to a deformation or a damaging of the hose and/or of a provided seal.

A screw element of the initially named kind is known from the DE 44 42 075 C1 and/or from the US 2007/0254744 and can be considered as a screw element having an installed torque limiter. The known designs in accordance with these documents are demanding in effort and cost with regard to their manufacture, since relatively filigree structures are required which complicate the injection molded tools used. Furthermore, the known designs are not really compact.

The object of the present invention lies therein to provide a screw element of the initially named kind which is not particularly demanding in effort and cost in its manufacture; however, is compact and can, for example, be produced at least generally of plastic in an injection molded process and which enables a reliable fastening and ensures the required torque also for limited spatial conditions.

In order to satisfy this object, a screw element of the initially named kind is provided which is characterized in that the installation limiting the torque has at least one ramp part which can rotate with the first or the second part in a direction in parallel to the longitudinal axis of the screw element with respect to a spring bias and cooperates with ratchet noses of the respective other part.

The ratchet noses can advantageously have the shape of ramps directly following one another or following one another with gaps in a ring arrangement, wherein an axial step is present between the trailing edge of the one ramp and the starting edge of the ramp following this. In this connection the designation "axial step" does not necessarily mean that the corresponding surfaces have to be aligned axially in parallel, but rather that the axial step itself can also be formed by an inclined surface or in a different manner (for example, by a curved surface). The number of ramps can be selected in dependence on the requirement. For only one ramp the said axial step lies between the trailing edge of the ramp and its starting edge, the torque limitation in this case is, however, not necessarily ideal, since a relatively large angle of rotation is required before the limitation comes into effect, such that the danger arises that the screw element can possibly be fastened to tight.

For this reason, a plurality of ramps are preferred, wherein the number of ramps should not be infinitely large, since then filigree structures would arise again. Up to twelve ramps are generally plausible without further ado.

A design of the screw element in accordance with the present teaching ensures the desired torque limitation by means of a force acting in an axial direction instead of forces acting in a radial direction, as is the case for the designs known in accordance with the above mentioned documents. For this reason screw elements in accordance with the invention can be built considerably more compact in comparison to the known screw elements for the same threaded size with respect to the radial dimensions. Furthermore, the screw elements in accordance with the invention can be produced cheaper through the avoidance of filigree features of shape which are difficult to manufacture. The spring part can be punched as a simple metal part from a sheet metal material which is not only simple in its manufacture, but it enables the precise determination of the axially acting forces, which finally limit the torque, in particular as metal parts can be produced with mechanical properties which have less of a spread than those of plastic parts.

It is particularly favorable when at least one dog is provided which serves for the rotation of the ramp part together with the first or the second part.

A preferred design of the ramp part lies therein in configuring this as a spring ring. In this connection the spring ring, for example, obtains the shape of a securing ring provided with serrated edges and is thus best suited for mass production.

In this connection the spring ring which can rotate with the first part or with the second part can be equipped with features of shape which are in engagement with complementary features of shape of the corresponding part and which act as dogs.

Features of shape of the ramp part and/or of the spring ring can preferably be selected cost-effectively from the group comprising axially directed openings, axially directed bores or punched holes, radially inwardly directed noses and radially outwardly directed noses. The complementary features of shape which are to be manufactured by an injection-molded process at the rotating part of the screw element are then selected from the group comprising axially directed posts matched to the shape of the openings, the bores or the punched holes, radially outwardly facing grooves at a cylindrical section of the part rotating the ramp part and radially inwardly facing grooves at an inner wall of the part entraining the ramp part.

In a preferred embodiment a spring part is provided between the ramp part and the first part or between the ramp part and the second part. In this embodiment an elastic component is thus provided between the ramp part and e.g. the second part in order to generate the desired torque limitation. The spring part can, e.g. be produced from metal and the ramp part can e.g. be produced from a plastic, for example in an injection-molded process. Thus, the desired torque can be set more precisely and a screw element in accordance with the invention can be manufactured even more cost-effectively.

The ramp part is then equipped with features of shape which are in engagement with complementary features of shape of the first or of the second part and which can act as dogs.

Preferably, the spring part is selected from the group comprising a coil spring, a disk spring, a spiral spring, a Belleville spring and a leaf spring.

In this connection the surface of the ramp part which abuts the rotating part or the spring part is planar which likewise enables a cost-effective manufacture of the ramp part.

In a corresponding manner the surface of the rotating part which abuts at the ramp part or the spring parts can be formed by a radial shoulder of the rotating part which is likewise simple to manufacture.

It is particularly favorable when the ratchet noses are configured at a second ring which is respectively rotationally fixedly connected to the respective other part or is connected via further dogs. In this connection the second ring can be configured comparatively stiff in comparison to the aforementioned spring ring or can likewise be configured as a spring ring. The ring can possibly have the same formation as the first mentioned spring ring which enables a particularly rational manufacture.

The solution having a second ring has the advantage that also the corresponding ratchet noses can be produced simply and with a very well defined shape.

The connection point between the first part and the second part of the screw element can advantageously be formed by at least one radial projection at the first part or at the second part and can be formed by at least one radial recess in the respective other part.

It is particularly favorable when the at least one radial projection is formed by a ring nose and the at least one radial recess is formed by a ring groove, since such features can be produced simply in an injection-molded process.

The invention further relates to a simplified embodiment comprising a screw element for fastening an article, for example having the shape of a plastic line to a counter-piece, such as a connector to a further line or a device connection, wherein the screw element is composed of a first part rotatable by hand or with a tool and of a second part provided with a thread, wherein the first part and the second part can be rotated relative to one another about the longitudinal axis of the screw element, but can be axially held to one another via a connection point, having the particular characteristic that the first part and the second part are each equipped with axial surfaces facing one another, each surface having at least one axially rising ramp and in that the connection point is configured in order to either limit or abruptly increase or abruptly decrease the axial holding force between the first part and the second part to limit a torque transmittable between them on a rotational movement thereof.

The above-mentioned examples have the advantage that the torque limitation on fastening the screw element is effective, but is not hindering on a release of the screw element. In this case the spring parts abut against the axial steps between the ratchet noses and thus enable a simple unscrewing of the screw element.

The maintenance of a predefined torque enabled by the invention ensures that, specifically for PTFE and FEP lines, the contact pressure is not so high that an undesired flow of the hose material arises. Furthermore, the support ring and possibly an O-ring provided between the support ring and the flange or an O-ring provided at a different position is protected against an excessive pressing together by means of the torque limitation.

The invention will be described in detail in the following by means of embodiments with reference to the drawing in which is shown:

FIGS. 1A and 1B two perspective illustrations and exploded illustrations of a screw element having a spring ring in accordance with the invention;

FIGS. 2A to 2D a top view (FIG. 2A), a side view (FIG. 2B), a sectional illustration (FIG. 2C) corresponding to the sectional plane A-A of the FIG. 2A and a perspective illustration (FIG. 2D) of the spring ring of the design in accordance with FIGS. 1A and 1B;

FIGS. 3A to 3D a top view (FIG. 3A), a side view (FIG. 3B), a sectional illustration (FIG. 3C) corresponding to the sectional plane A-A of the FIG. 3A and a perspective illustration (FIG. 3D) of one part (of the screw cap) of the design in accordance with FIGS. 1A and 1B.

FIGS. 4A to 4D a top view (FIG. 4A), a side view (FIG. 4B), a sectional illustration (FIG. 4C) corresponding to the sectional plane A-A of the FIG. 4A and a perspective illustration (FIG. 4D) of the assembled screw element of the design in accordance with FIGS. 1A and 1B.

Figure 5A:
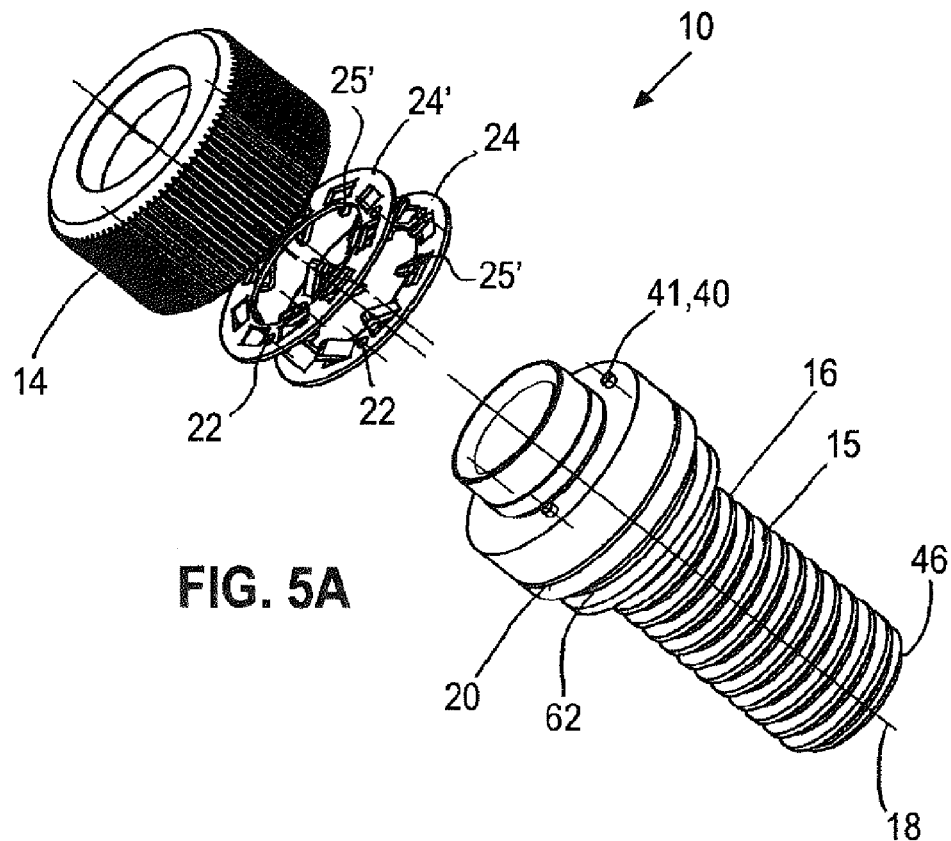
Figure 5B:
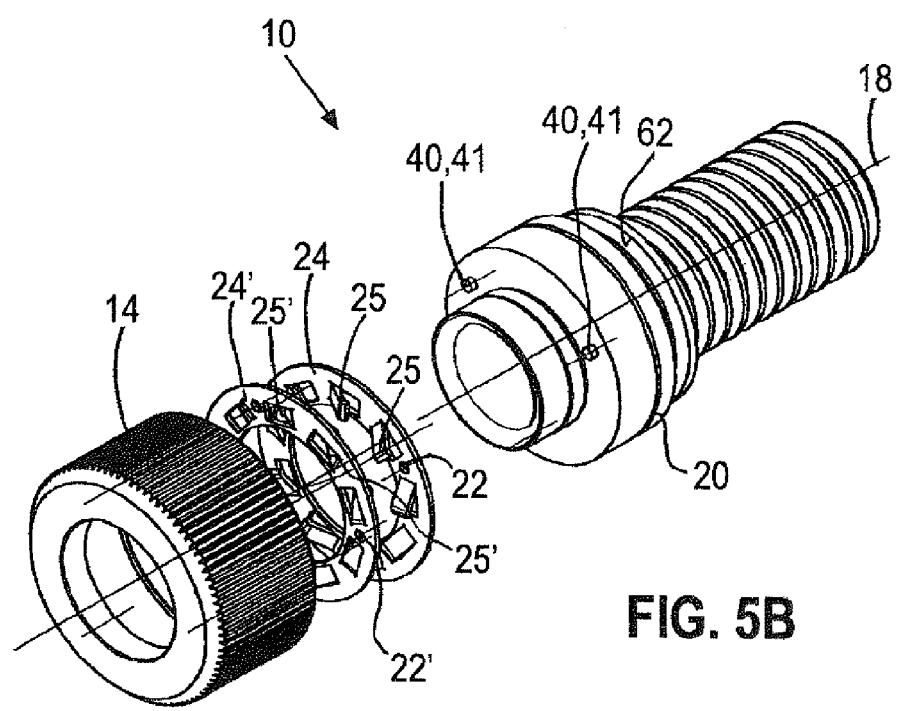
Figure 7A:
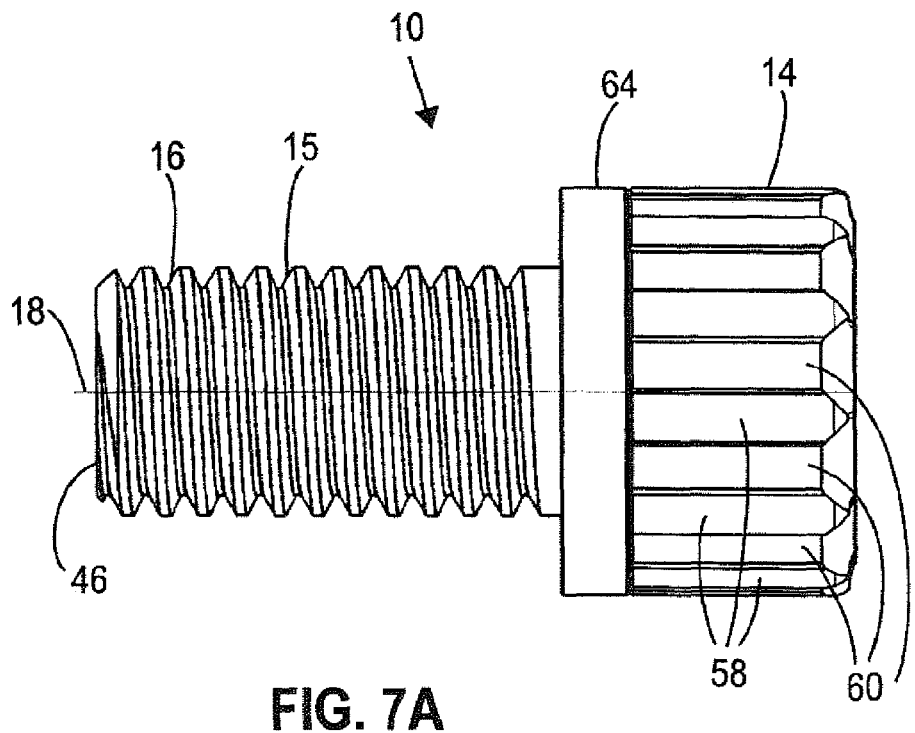
Figure 7B:
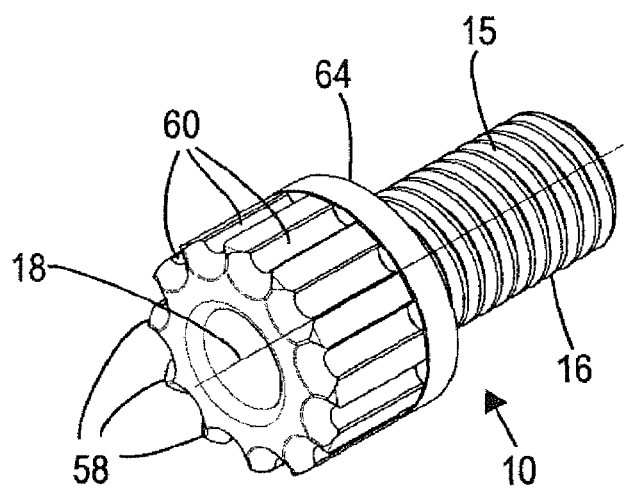

FIGS. 5A to 5B and 6A to 6D illustrations corresponding to those of the FIGS. 1A and 1B and 3A to 3D, but of a screw element in accordance with the invention having two spring rings, wherein the sectional illustration in accordance with FIG. 6C corresponds to a section of the plane A-A of the FIG. 6B;

FIGS. 7A and 7B illustrations of a screw element in an assembled state representing the above explained screw elements, but having a different head shape, this means with a design of the cap part of the screw elements of the FIGS. 1A and 1B and/or of the FIGS. 5A and 5B; and FIGS. 8A and 8B a further embodiment of a screw element in accordance with the invention having a spring ring in two perspective exploded view illustrations.

The FIGS. 1A and 1B, 2A to 2D, 3A to 3D and 4A to 4D respectively show a screw element 10 for fastening an article, for example, having the shape of a plastic line 12 (FIG. 4C) to a counter-piece 38 (FIG. 4C), such as a connector to a further line or to a device connection, wherein the screw element 10 is composed of a first part 14 rotatable by hand or with a tool and of a second part 16 provided with a thread 15. The first part 14 and the second part 16 can be rotated relative to one another about the longitudinal axis 18 of the screw element 10, but can be axially held to one another via a connection point 20. The screw element 10 is further composed of an installation limiting a torque transferred from the first part 14 to the second part 16 which installation limiting the torque comprises at least one spring part 24. In this example the spring ring 24 can be rotated with the second part 16 bearing the thread 15, this means it is rotationally fixedly connected to this. The spring ring 24 is provided with spring tongues 25 which extend inclined with respect to the plane of the spring ring and in a direction in parallel to the longitudinal axis 18 of the screw element, this means that they can deflect axially as will be explained in detail in the following.

The spring ring 24 and/or its spring tongues 25 work and/or cooperate with ratchet noses 26 of the respective other part 14. The present spring ring has three connection points or features of shape 22 by means of which it is rotationally fixedly connected to the second part 16 bearing the thread 15.

The ratchet noses 26 in this example have the shape of ramps 30 following one another with gaps 28 in a ring arrangement, wherein an axial step 36 is present between the trailing edge 32 of the one ramp 30 and the starting edge 34 of the ramp 30 following this. The number of ramps 30 in this connection is nine, can, however, be selected in dependence on the actual requirement. For only one ramp 30 the said axial step 36 lies between the trailing edge 32 of the ramp 30 and its starting edge 34. For only one ramp 30 the torque limitation would not necessarily be ideal, since a relatively large angle of rotation would be required before the limitation would take effect, such that the danger would arise that the screw elements 10 would possibly be fastened too tight.

For this reason, a plurality of ramps 30 are preferred, wherein the number should not be infinitely large, since then filigree structures would in turn arise. Up to twelve ramps 30 can presumably be used without further ado.

In order to ensure that the spring ring rotates with the second part 16 bearing the thread 15, three dogs 40 in the shape of cylindrical posts or pins 41 are provided in this example which pins cooperate with the features of shape 22 and which serve for the rotation of the spring ring 24 with the second part 16. Three dogs would not necessarily have to be provided. Under some circumstances one dog would be sufficient, two would be better and more than three are generally possible but are not necessarily required.

The pins or posts 41 are simultaneously configured on the manufacture of the second part 16 by means of an injection molded process in such a way that a uniform part, this means a one piece part is present. It would also be plausible to provide separate pins which can be inserted into bores of the second part.

The ratchet noses 26 can advantageously have the shape of ramps 30 directly following one another or following another with gaps in a ring arrangement, wherein an axial step 36 is present between the trailing edge 32 of the one ramp 30 and the starting edge 34 of the ramp 30 following this. In this connection, the number of ramps 30 can be selected in dependence on the actual requirement. This number also corresponds to the number of spring tongues 25 which have the same angular spacing and at least substantially have the same radial dimensions as the ramps 30, but the spring tongues 25 are slightly smaller in the radial direction than the ramps 30.

With only one ramp 30 the said axial step 36 lies between the trailing edge 32 of the ramp 30 and its starting edge 34, the torque limitation is, however, in this case is also not necessarily ideal, since a relatively large angle of rotation is required before the limitation takes effect in such a way that the danger arises at the screw element 10 that they could possibly be fastened too tight.

For this reason a plurality of ramps 30 are preferred, wherein the number should not be infinitely large, since then again filigree structures would arise. Up to twelve ramps 30 are presumably acceptable without further ado and without limitation.

However, it would also be possible to provide the ramps and/or the ratchet noses 30 at the second part 16 bearing the thread 15 and to arrange the dogs 40 in the first part 14, this means in the cap, as is shown in the FIG. 6A.

As is evident from the statements made above, the spring part 24 is preferably configured as a spring ring; however, could also be designed differently, for example, by individual leaf springs or hair pin valve springs distributed about the circumference.

As already discussed, the spring ring 24 rotatable with the second part 16 is equipped with features of shape 22 which are in engagement with complimentary features of shape 41 of the corresponding part 16 and which act as a dog 40.

Many possible alternatives are available for the dogs 40 and for the features of shape 22 of the spring ring 24 cooperating therewith.

In the shown embodiment the features of shape 22 of the spring ring 24 are axially directed openings in the shape of circular, axially directed punched holes and these cooperate with cylindrical, axially aligned posts 41 at the second part 16.

The punched holes 22 can, however, also be bores which are, for example produced by a drill (not shown) or by a laser (not shown). It is also not necessarily required that the cross-sectional shape of the dog and/or of the pins 41 are matched to the shape of the punched holes 22 or bores 22, they must merely fit into the corresponding punched holes 22 and/or bores 22. It is also not required that the punched holes 22 or the other types of openings 22 are circular. Also different shapes such as polygonal cross-sectional shapes are possible.

A further possibility consists therein in realizing the features of shape 22 by means of radially inwardly directed noses of the spring ring 24 which engage in radially outwardly directing recesses in a centrally arranged projection (not shown) of the part 16 bearing the thread 15 (or at the "cap" 14).

Also radially outwardly directed noses of the spring ring 24 would come into question which are arranged in radially inwardly facing recesses in an internal wall of a part entraining the spring ring 24. Such an inner wall could be formed by the inner wall of the "cap" 14 or by a hollow projection (not shown) of the part 16 bearing the thread 15.

Furthermore, a reverse arrangement would be possible in which the noses engage at the inner wall of the "cap" 14 (not shown) or of a hollow projection (not shown) of the part 16 bearing the thread 15 (likewise not shown) in grooves or in recesses of the spring ring 24.

As is particularly evident from the FIGS. 2A to 2D, the surface 23 of the spring ring 24 which abuts the rotating part is of planar design. Correspondingly, the surface of the rotating part 16 at which the spring ring contacts, this means in this example the surface 52 of the end face 54 of the part 16 bearing the thread 15 is formed by a planar surface of the rotating part 16 defining a radial shoulder.

As is evident from the FIGS. 4A to 4D the radially inwardly directed ring nose is in engagement at the inner wall of the "cap" 14 with the radially outwardly directed groove of the part 16 bearing the thread 15 in the assembled state of the screw element 10, whereby the spring ring 24 is held at the said radial shoulder 52 and is in engagement with the ratchet noses 30.

In this example, the line 12 is composed of plastic and is provided with a flange 42 at its end facing the screw element 10, which flange is typically produced by molding and/or pressing the cutoff end of the line 12 over in a heated state. For the screwing of the screw element 10 to a connection 38 of a housing or to a connection piece, the flange 42 is caught between a support ring 44 at the end face of the free end 46 of the screw element 10 and a shoulder 48 at an end of a threaded bore 50 of the connection 38.

When the screw element 10 is fastened, be it by hand or with a tool, the torque increases with the increasing engagement of the free end 46 of the part 16 bearing the thread 15 having the support ring 44 and the flange 42 at the end of the line 12. As soon as the free end 52 of the flange 42 abuts at the shoulder 48 of the corresponding connection the ramps 30 start to glide over the spring tongues 25 of the spring ring 24 and press these more and more in the direction of a leveled state in the plane of the surface 54. In this respect the inclined surfaces of the ramp 30 lie approximately in parallel to the spring tongues 25 in the relaxed state of the spring ring 24.

As soon as the leveled state of the spring tongues 25 is achieved the free ends 56 of the spring tongues 25 jump over the axial steps 36, the axially acting spring force seizes and the "cap" 14 can be turned further via the part 16 bearing the thread 15 with a merely noticeable resistance, when the base surfaces of the gaps 28 glide over the free end 56 of the spring tongues 25. A planar surface 35 is present in this example between the trailing edge of each ramp 30 and the associated axial step 36 which surface lies in a radial plane with regard to the longitudinal axis 18. Such planar surfaces 35 can also be omitted, however, simplify the assembly of the screw element 10. While the free ends of the spring tongues 25 glide over the planar surface 35, the torque at least substantially remains constant. Thereafter, on a turning further of the "cap" 14, the spring tongues jump back into their inclined position. The torque abruptly decreases and stays at a low level up until the spring tongues 25 are again compressed following a further angle of rotation corresponding to the length of the gaps from the ramps 30. The applied torque increases again up until the maximum torque is again achieved at which the free ends 56 of the spring tongues 25 again lie aligned with the axial steps 36. Then the torque reduces again.

This game is repeated for so long as the cap is turned further. The part 16 bearing the thread 15 of the screw element 10 can, however, not be turned further, this means that it cannot be tightened any further and the maximum achievable torque is limited for this reason and indeed is limited to the technically desired value which depends on the stiffness of the material and the threaded shape and size, as well as on the selection of the number of spring tongues 25, the angle of the ramps 30, the stiffness of the material of the spring ring 24 and the dimensions of the spring tongues 25. Typically a clicking sound and a noticeable vibration also arises each time, when the spring tongues 25 relax at the positions of the axial steps 36 which together with the cyclically increasing torque are perceived by a user as a sign that the maximum torque is achieved. Since the torque is limited the screw element cannot be tightened too tight.

As is indicated above, a reversed arrangement can be selected, this means that the ratchet noses forming ramps 30 are arranged at the part 16 of the screw element bearing the thread 15 and the dogs 40 are arranged at the "cap" 14, so that the torque limitation arises in analogy to that stated above.

A further embodiment of the screw element 10 in accordance with the invention will now be described with reference to the FIGS. 5A and 5B as well as with reference to FIGS. 6A to 6D. In these Figures the same reference numerals are used for corresponding parts or parts having a corresponding function as used so far and it is understood that the above-described is also true for these embodiments, as well as for other embodiments. Only parts or concepts deviating therefrom will be described in more detail.

Two spring rings 24 and 24' are used in the embodiment in accordance with FIGS. 5A and 5B, wherein the spring rings 24 are coupled to the part 16 bearing the thread 15 by means of dogs 40, as was so far the case, while the spring ring 24' is turned with the "cap" 14 by means of further dogs 40'. The spring tongues 25' of the spring ring 24' which in this example is identical to the spring ring 24 which in turn corresponds to the spring ring 24 of the FIGS. 2A to 2D, in this example form the ramps 30, this means the ratchet noses in such a way that it is not required in this example—in the first example of the ramps 30—to form these in the same injection mold as the "cap" itself. For this reason, the "cap" 14 in this example has a planar surface corresponding to the planar surface of the previous embodiments. This is not only of advantage in the sense that the injection mold is simplified and has even less filigree structures, but it is also simpler to predefine the technical properties of the screw with reference to the limitation of the torque and to the gliding of the spring tongues 25' of the spring ring 24' over the spring tongues 25' of the spring ring 24', since spring steel has more precise properties to be maintained.

In other words, the ratchet noses are formed at the second ring 24 in this example, which is rotationally fixedly connected to the part 14, for example via corresponding dogs 40'.

However, it is not necessarily required that the second ring 24' is likewise configured as a spring ring and even less that it should have the same design as the first mentioned spring ring 24. For example, the ring 24' could be configured as a stiff substantially non-elastic ring or it could have a different stiffness than the spring ring 24.

The connection point between the "cap" 14 and the part bearing the thread 15 is formed by at least one radial projection at the first part 14 (or at the second part 16) and at least one radial ring recess in the respectively other part 16 and/or 14 also for this embodiment.

The radial projection in this example, as like for the first example, is preferably formed by a ring nose and the at least one radial recess is formed by a ring groove. Other designs would, however, also be possible, for example, a plurality of radial projections distributed over the circumference could engage into a ring recess.

The FIGS. 6A and 6B show a screw element which corresponds to that of the previous examples, apart from the fact that the "cap" 14 is provided with pronounced longitudinal ribs and longitudinal grooves 60 at its outer side rather than with fine longitudinal ribs 58 and longitudinal grooves 60. The fine longitudinal ribs 58 and longitudinal grooves 60 are suitable for a manual fastening of the screw element 10, while the pronounced longitudinal grooves 58 and longitudinal grooves 60 are better suited for the application of a tool (not shown) for fastening the screw element 10. The outer shape of the cap 14, however, can also be realized in a different manner, for example, as an outer hexagonal shape.

The reference numeral 62 indicates a ring groove 62 or ridge 62 which is provided for the reception of a colored coding ring 64 known per se which is shown in the FIGS. 7A and 7B and which sits in the ring groove 62 and/or at a ring shoulder of the screw element 10 at a side of the head of the screw element 10 facing the thread 15.

The present examples were described by means of a screw element 10 in the shape of a hollow bolt element 10. However, the invention could also be realized with a corresponding sleeve nut. For a sleeve nut, the first part 14 is formed by a cap and the second part 16 bearing the thread would be formed by a hollow component provided with an internal thread, wherein a spring ring and ratchet noses as were previously described act between the first part 14 and the second part 16.

The FIGS. 8A and 8B likewise show a screw element 10 for fastening an article, for example, having the shape of a plastic line 12, to a connector to a further line or to a device connection, wherein the screw element 10 is composed of a first part 14 rotatable by hand or with a tool and of a second part 16 provided with a thread 15. The first part 14 and the second part 16 can be rotated relative to one another about the longitudinal axis 18 of the screw element 10, but can be axially held to one another by a connection point 20. In these Figures the same reference numerals are used for corresponding parts or parts having a corresponding function, as were previously used and it is understood that the above-described is also true for these embodiments such as also for other embodiments. Only parts or concepts deviating therefrom are described in detail.

The screw element 10 of FIGS. 8A and 8B are further composed of an installation limiting a torque transferred from a first part 14 to the second part 16 which comprises at least a spring part 66. In this example, a coil spring 66 is arranged between the ramp part 24 and the second part 16 bearing the thread 16. The ramp part is connected to the second part 16 via the dogs 40 in a rotationally fixedly manner.

The ramp part 24 is provided with ramps 25 in analogy to the spring part 24 of the FIGS. 1A and 1B which run inclined with regard to the plane of the spring ring and in a direction in parallel to the longitudinal axis 18 of the screw element, this means that they can deflect axially by means of the spring part 66. The ramp part 24 of the FIGS. 8A and 8B is thus not designed as an elastic component in comparison to the previous Figures, but rather as a comparatively stiff component e.g. a plastic component, which is produced in an injection molded process which at least substantially does not deform with the forces to be expected in this case. In order to nevertheless enable the required relative movement between the ramp part 24 and the ratchet noses 26 provided at the first or the second part 14, 16 of the screw element 10 a coil spring 66 is used in this example.

Such a spring part 66 can, as the person of ordinary skill in the art knows, also be selected from the group comprising a disk spring, a spiral spring, a Belleville spring and a leaf spring.

LIST OF REFERENCE NUMERALS

10 screw element
12 line
14 part
15 thread
16 part
18 longitudinal axis
20 connection point
22 shape feature, connection point
23 surface
24, 24' spring part
25, 25' spring tongue
26 ratchet nose
28 gap
30 ramp
32 trailing end
34 starting end
35 surface
36 step
38 connection
40, 40' dog
41 pin
42 flange
44 support ring
46 free end
48 shoulder
50 threaded bore
52 end face
54 surface
56 free end
58 longitudinal rib
60 longitudinal groove
62 ring groove
64 coding ring
66 spring part

The invention claimed is:

1. A screw element for fastening an article to a counter-piece, wherein the screw element is composed of a first part rotatable by hand or with a tool and of a second part provided with a thread, wherein the first part and the second part can be rotated relative to one another about a longitudinal axis of the screw element, but can be held axially to one another via a connection point, as well as being composed of an installation limiting a torque transferred from the first part to the second part, wherein the installation limiting the torque has at least one ramp part which can rotate with the first part or with the second part, the installation limiting the torque is movable in a direction in parallel to the longitudinal axis of the screw element with respect to a spring bias and cooperates with ratchet noses of the respective other one of the first part or the second part.

2. The screw element in accordance with claim 1, wherein the article has the shape of a plastic line.

3. The screw element in accordance with claim 1, wherein the counter piece is one of a connector to a further line and a device connection.

4. The screw element in accordance with claim 1, wherein at least one dog is provided which serves for a rotation of the ramp part together with the first part or the second part.

5. The screw element in accordance with claim 1, wherein the ramp part which can rotate together with the first part or with the second part is equipped with features of shape which are in engagement with complementary features of shape of the corresponding part and which act as dogs.

6. The screw element in accordance with claim 5, wherein the features of shape of the ramp part are selected from the group comprising axially directed openings, axially directed bores or punched holes, radially inwardly directed noses and radially outwardly directed noses; and the complementary features of shape are selected from the group comprising axially directed posts matched to the shape of the openings, the bores or the punched holes, radially outwardly facing grooves at a cylindrical section of the part entraining the spring ring and radially inwardly facing grooves at an inner wall of the part entraining the spring ring.

7. The screw element in accordance with claim 1, wherein the connection point is formed by at least one radial projection at the first part or at the second part and wherein at least one radial recess is formed in the respective other one of the first part or the second part.

8. The screw element in accordance with claim 7, wherein the at least one radial projection is formed by a ring nose and the at least one radial recess is formed by a ring groove.

9. The screw element in accordance with claim 8, wherein the surface of the rotating part abuts the ramp part or the spring part and is formed by a radial shoulder of the rotating part.

10. The screw element in accordance with claim 1, wherein a spring part is provided between the ramp part and the first part or between the ramp part and the second part.

11. The screw element in accordance with claim 10, wherein the spring part is selected from the group comprising a coil spring, a disk spring, a spiral spring, a Belleville spring and a leaf spring.

12. The screw element in accordance with claim 11, wherein the second ring is likewise configured as a spring ring.

13. The screw element in accordance with claim 12, wherein the second ring is likewise configured as a spring ring and has the same formation as the first mentioned spring ring.

14. The screw element in accordance with claim 1, wherein the ramp part is configured as a spring ring.

15. The screw element in accordance with claim 1, wherein the surface of the ramp part which abuts the rotating part or the spring part is planar.

16. The screw element in accordance with claim 1, wherein the ratchet noses are configured at a second ring which is respectively rotationally fixedly connected to the respective other part or is connected via further dogs.

17. A screw element for fastening an article to a counter-piece, wherein the screw element is composed of a first part rotatable by hand or with a tool and of a second part provided with a thread, wherein the first part and the second part can be rotated relative to one another about a longitudinal axis of the screw element, but can be axially held to one another via a connection point, wherein the first part and the second part are each equipped with axial surfaces facing one another, each surface having at least one axially rising ramp; and wherein the connection points is configured in order to either limit or abruptly increase or abruptly decrease an axial holding force between the first part and the second part to limit a torque transmittable between them on a rotational movement.

18. The screw element in accordance with claim 17, wherein the article has the shape of a plastic line.

19. The screw element in accordance with claim 17, wherein the counter piece is one of a connector to a further line and a device connection.

\* \* \* \* \*